United States Patent [19]

Heller et al.

[11] Patent Number: 5,131,380
[45] Date of Patent: Jul. 21, 1992

[54] SOFTWALL MEDICAL TUBE WITH FIBEROPTIC LIGHT CONDUCTOR THEREIN AND METHOD OF USE

[76] Inventors: Richard M. Heller, 421 Ellendale Dr., Nashville, Tenn. 37205; Thomas F. Lachner, 321 Vincent Ct., Lake Bluff, Ill. 60044

[21] Appl. No.: 714,606

[22] Filed: Jun. 13, 1991

[51] Int. Cl.$^5$ ............................................. A61B 1/06
[52] U.S. Cl. ............................................. 128/6; 128/11
[58] Field of Search ........................... 128/6, 7, 8, 9, 11

[56] References Cited

U.S. PATENT DOCUMENTS

| | | | |
|---|---|---|---|
| 1,704,764 | 3/1929 | Schellberg . | |
| 2,487,498 | 11/1949 | Wallace | 128/7 |
| 3,760,797 | 9/1973 | Stauffer | 128/6 |
| 3,776,222 | 12/1973 | Smiddy | 128/6 |
| 3,817,619 | 6/1974 | Kawahara | 128/6 |
| 3,818,902 | 6/1974 | Kinoshita et al. | 128/6 |
| 4,096,862 | 6/1978 | De Luca | 128/348 |
| 4,244,362 | 1/1981 | Anderson | 128/200.26 |
| 4,267,828 | 5/1981 | Matsuo | 128/6 |
| 4,444,185 | 4/1984 | Slugar | 128/11 |
| 4,461,283 | 7/1984 | Doi | 128/7 |
| 4,567,882 | 2/1986 | Heller | 128/6 |
| 4,630,598 | 12/1986 | Bonnet | 128/7 |
| 4,758,222 | 7/1988 | McCoy | 128/6 |
| 4,776,844 | 10/1988 | Ueda | 128/6 |
| 4,798,193 | 1/1989 | Giesy et al. | 128/7 |
| 4,800,870 | 1/1989 | Reid, Jr. | 128/6 |
| 4,815,450 | 3/1989 | Patel | 128/6 |
| 4,921,326 | 5/1990 | Wild et al. | 128/6 |
| 4,979,498 | 12/1990 | Oneda et al. | 128/6 |

OTHER PUBLICATIONS

Vollmer et al., Annals of Emergency Medicine, vol. 14, No. 4 (Apr. 1985).
Rayburn, Anaethesia, vol. 34, pp. 677-678 (1979).
Foster, Anaesthesia, vol. 32, p. 1038 (1977).

*Primary Examiner*—Paul J. Hirsch
*Attorney, Agent, or Firm*—Tilton, Fallon & Lungmus

[57] ABSTRACT

The combination of a transparent medical tube and a flexible light conductor slidably and removably disposed therein, and the method of use of that combination. The medical tube is formed of relatively soft, highly-flexible, thermoplastic material and has an open proximal end and a distal end wall with sidewall openings adjacent thereto. The light conductor fits closely within the lumen of the medical tube, with its distal end disposed adjacent to the tube's distal end wall and a handle at its proximal end coupled to the proximal end of the tube. Because of its greater stiffness, the conductor facilitates insertion of the tube/conductor combination without buckling or independent twisting of the tube; however, because the two are secured together at their proximal ends, torquing forces applied to the handle of the conductor are transmitted to the tube for aiding in directing and advancing the tube/conductor combination. Light transmitted by the conductor to its distal end passes outwardly through the medical tube's distal end wall and may be visually and externally observed through the body wall of the patient.

11 Claims, 1 Drawing Sheet

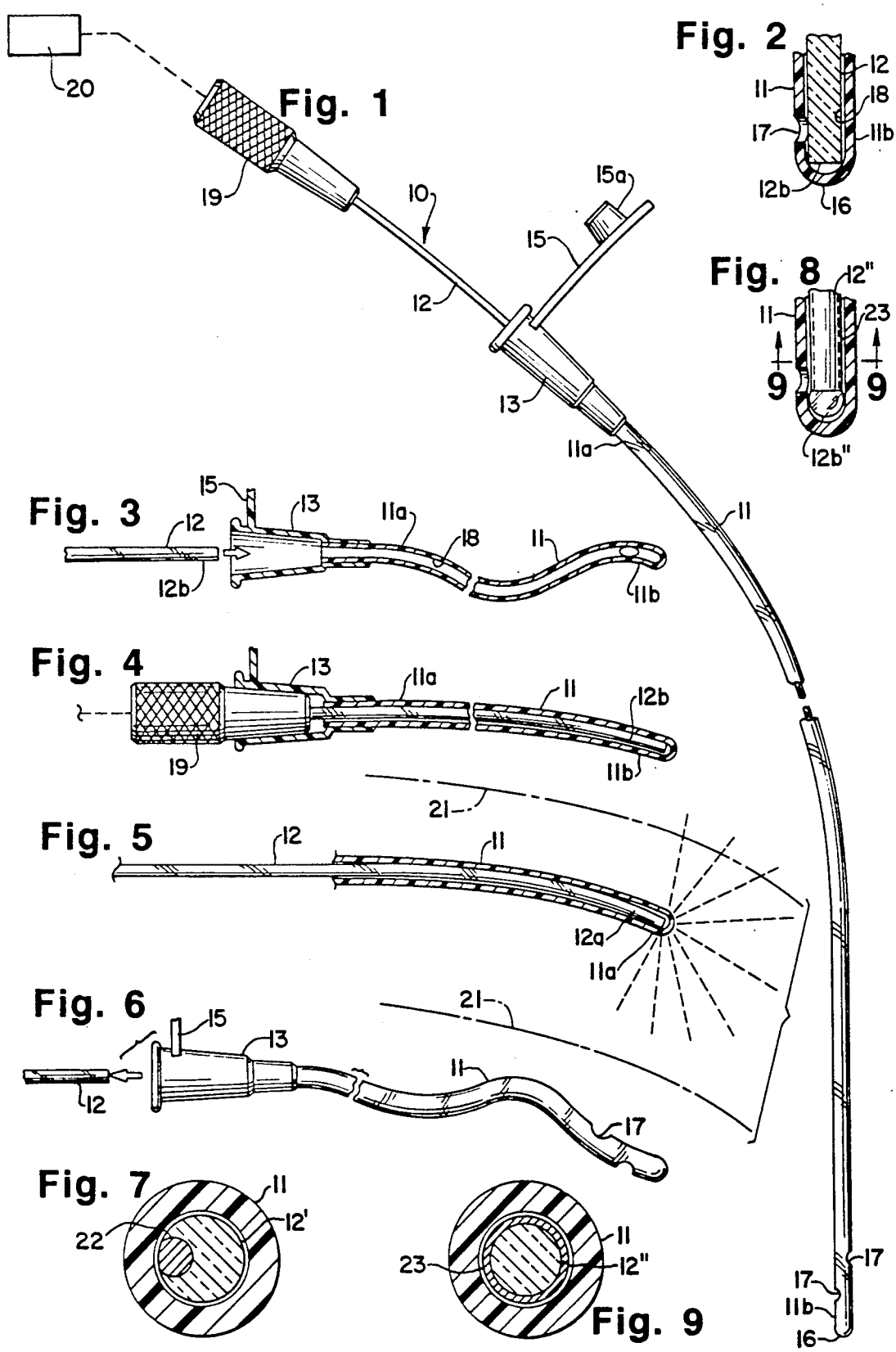

SOFTWALL MEDICAL TUBE WITH FIBEROPTIC LIGHT CONDUCTOR THEREIN AND METHOD OF USE

BACKGROUND AND SUMMARY

Heller U.S. Pat. No. 4,567,882 discloses an endotracheal tube having a fiberoptic light conductor extending lengthwise through the transparent wall thereof. The conductor ends in a light-emitting terminus adjacent the tube's distal end, and light emitted laterally from the tip of the medical tube may be visually and externally observed through the body wall of a patient for accurately and quickly determining the anatomical location of that tip.

Other devices and methods for transillumination have been disclosed in the prior art. Schellberg U.S. Pat. No. 1,704,764 discloses transillumination through the wall of the colon by inserting a light bulb into a transparent catheter after the catheter is in place. Others have used bendable light wands or light-transmitting cables to aid in the placement of open-ended endotrachael tubes to guide the placement of such tubes by transillumination. See Vollmer, T. P. et al Annals of Emergency Medicine, Vol. 14, No. 4 (April 1985); Rayburn, R. L., Anaesthesia, Vol. 34, pp. 677-8 (1979); Foster, C. A., Anaesthesia, Vol. 32, p. 1038 (1977).

The use of stylets to guide the placement of catheters, especially tubes for the administration of parenteral fluids, is also well known. Anderson U.S. Pat. No. 4,244,362 discloses the use of a flexible stylet for guiding the placement of an endotrachael tube.

Other references indicating the state of the art are Smiddy U.S. Pat. No. 3,776,222 and DeLuca U.S. Pat. No. 4,096,862.

In some medical applications it is desirable to use a medical tube formed of relatively soft, highly-flexible material, especially where such a tube must contact delicate tissues or remain in place for extended periods. A nasogastric tube is one example; a peritoneal dialysis catheter is another. Medical tubes for evacuating fluids from the plural cavity, or tubes for subcutaneous abscess drainage, preferably have similar characteristics. Tubes intended for such uses generally have distal end portions with a plurality of side openings and are provided with transverse walls at their extreme distal ends so that the openings are less likely to become obstructed in use. Because of their relatively soft, floppy character, such tubes may be difficult to direct, advance, and position properly within the body without becoming twisted, folded, or kinked.

Accordingly, one aspect of this invention lies in recognizing that a fiberoptic light conductor may provide an ideal stiffening and torquing element for a relatively floppy medical tube if the light conductor extends substantially the full length of the tube, is coupled to the tube at its proximal end, and also preferably engages the inside surface of the tube at least at its distal end. The light conductor and tube therefore move together as a unit. This facilitates ease of positioning of the tube as both may be twisted or torqued in one motion. Not only does the fiberoptic light conductor add the requisite degree of stiffness and torquability to the tube to facilitate its directional control during insertion and placement, preventing undesirable kinking or independent twisting of the tube, but light may be transmitted through the conductor to its distal end for purposes of transillumination through the body wall of the patient.

Light emanating from the end face or faces of the conductor passes through the distal end wall of the transparent medical tube and may be externally observed through the body wall of the patient as a spot of light. Following proper placement, of the medical tube, the light conductor is withdrawn from the medical tube through its open proximal end, and the tube is then utilized for the intended medical procedure.

Briefly, the combination of this invention takes the form of a transparent medical tube and a flexible fiberoptic light conductor slidably and removably disposed therein, the term "transparent" being used here to mean light transmissible and therefore including the use of materials that are not necessarily clear and may even be translucent. Coupling means are provided at the proximal ends of the tube and insertable light conductor to secure them together against independent relative rotation. With the light conductor removed from its lumen, the medical tube is highly flexible or floppy, being formed of soft thermoplastic material. The light conductor is flexible but relatively stiff in comparison with the medical tube. A smooth glass fiber, or a cylindrical bundle of such fibers for larger size tubes, is particularly effective. So that twisting or torquing forces may be transmitted from the light conductor to the medical tube during an insertion procedure, the light conductor should be dimensioned to fit closely but slidably within the lumen of the tube.

Other features, advantages, and objects will appear from the specification and drawings.

DRAWINGS

FIG. 1 is a side elevational view of a combination medical tube and light conductor embodying the present invention, the conductor being shown partially inserted into the tube.

FIG. 2 is an enlarged fragmentary longitudinal sectional view illustrating the distal tip of the tube with the light conductor fully inserted therein.

FIGS. 3-6 illustrate a sequence of method steps in the use of the combination.

FIG. 7 is an enlarged cross sectional view of a second embodiment.

FIG. 8 is an enlarged, fragmentary, longitudinal sectional view similar to FIG. 2 but illustrating a third embodiment of the invention.

FIG. 9 is a still further enlarged cross sectional view taken along line 9-9 of FIG. 8.

DETAILED DESCRIPTION OF PREFERRED EMBODIMENTS

Referring to the drawings, the numeral 10 generally designates an assembly comprising a medical tube 11 and a flexible light conductor 12. Tube 11 is of uniform cross sectional dimensions along substantially its entire length and may be provided with an adaptor 13 at its proximal end 11a. As shown most clearly in FIG. 3, the open proximal end of the tube may extend into the tubular adaptor and be secured therein by cement or by any other suitable means. Depending on the particular use of tube 11, the adaptor 13 may be connected to a mating connector or tube leading to a fluid source, a suction unit, a drainage pouch, or any other suitable medical device. An integral strap 15 equipped with a plug 15a (FIG. 1) may be used to close the opening of the adaptor when light conductor 12 is removed and tube 10 is not in use.

At its distal end 11b, the tube 11 is preferably closed, being provided with a rounded tip defined by end wall 16. A plurality of sidewall openings 17 are provided adjacent thereto for inflow or outflow of fluids.

The tube 11 is formed from a soft, transparent (including translucent) plastic material with the result that the tube may be characterized as highly flexible or bendable, even floppy. It has enough inherent form retention to maintain an open lumen in use, in the absence of exceptional forces, but is soft and yieldable enough to avoid injury to delicate tissues. Polyvinyl chloride is a typical material from which such a tube may be formed, but other polymeric materials having similar properties may be used.

In the drawings, tube 11 is depicted as a conventional nasogastric feeding tube, but it is to be understood that the combination of this invention may utilize tubes having the properties already described but intended for different purposes and, as such, having different dimensions and proportions. Thus, tube 11 may also take the form of a tube intended for peritoneal dialysis, or for evacuating fluids from the plural cavity, or for subcutaneous abscess drainage. In each case such a tube must be formed from soft, transparent plastic material, be highly flexible or bendable, and have a distal end with one or more openings.

The light conductor 12 takes the form of an elongated, flexible, fiberoptic strand or cable. It is formed from glass or a relatively rigid, light-conductive polymeric material such as methyl methacrylate and, as such, is considerably less flexible than tube 11. It has uniform outside dimensions throughout its full length and its diameter is only slightly less than the diameter of lumen 18 of tube 11. The insertable length of the fiberoptic light conductor 12 is the same as, or slightly less than, the length of lumen 18, and a mating coupling element 19 is provided at its proximal end. Element 19 is shown in the drawings as having a Luer taper and is dimensioned to be frictionally received in the tapered socket of adapter 13 when the two are fitted together as depicted in FIG. 4. Under such conditions, with the conductor fully inserted, the distal end 12b of the light conductor is located adjacent the distal end wall 16 of medical tube 11 (FIG. 2).

While it has been found highly effective to form the distal end 12b of the light conductor with an end face extending in a plane normal to the longitudinal axis of the conductor, as illustrated in FIG. 2, it is to be understood that variations may also be suitable. For example, the conductor may have a beveled end face, as disclosed in the aforementioned U.S. Pat. No. 4,567,882, or it may be rounded and enlarged at its end as shown in FIG. 8.

Coupling element 19 is adapted for attachment either directly or by means of a suitable extension to a conventional light source 20. The light source is diagrammatically depicted in the drawings and may take the form of light boxes disclosed, for example, in U.S. Pat. Nos. 4,025,776 and 3,831,017. One effective light source utilizes a 150 watt incandescent light and is commercially available from Olympus Corporation of America, New Hyde Park, N.Y., under the designation ILK-3; however, other similar light boxes or light sources capable of generating light within the wavelength range of 250 to 2200 nanometers may be used.

The assembling of the medical tube 11 and light conductor 12 preferably occurs at the time of manufacture so that the components are supplied to a user in sterile, fully-assembled condition as depicted in FIG. 4 but, if desired, the components may also be supplied separately and assembled immediately prior to use. In either case, the distal end 12b of the light conductor is inserted into the lumen of the medical tube until it is coterminous with the distal end of the tube and coupling element 19 is secured to adapter 13 (FIGS. 3, 4). The insertion of the light conductor stiffens or reinforces the floppy tube with the controlled flexibilty of the combination greatly facilitating insertion into a patient's body through the mouth, nose, or surgically-formed opening without kinking, collapsing, or independent twisting or rotating of the tube.

Prior to such insertion into the body, the light conductor is coupled to light source 20 and the light source is energized. Thereafter, during insertion of the tube into a patient's body through a natural orifice, surgically-formed opening, or opening formed by trauma, light emitted from the distal end 12b of the conductor and passing through the transparent distal end wall 11b of the tube radiates outwardly and may be externally observed as a spot or bead of light through the body wall of a patient. In FIG. 5, the body wall is schematically represented by phantom line 21. It has been found that an observer need not be in direct endwise alignment with the light conductor in order to see the light emanating from the end of the conductor because tissues contacted by, or immediately adjacent to, the distal end 11b of the medical tube are illuminated by and reflect the emitted light. The end wall 11b of the medical tube contributes in causing some lateral redirection of the light discharged from the distal end of the conductor. By observing the advancement of the spot of light through the body wall, and by noting its intensity and size, medical personnel may control and confirm the placement of the tube. Rotational forces applied to the coupling element 19, which functions as a handle for exerting torquing as well as axial forces, help to orient the distal ends of the conductor/tube combination during such insertion. Once the medical tube is in place, with its tip at the desired location, the light conductor is removed, allowing the highly-flexible medical tube 11 to bend and flex in conformity with the site of insertion or implantation (FIG. 6). Reinsertion of the conductor may of course be undertaken should it later become necessary or desirable to confirm the location of the tube, determine whether it has moved over a period of time, or relocate and reposition its distal end.

For certain applications, it may be desirable if the light conductor, in addition to stiffening the medical tube and emitting light from the distal end of that tube, also were capable of accepting and retaining a preset curvature developed by the medical personnel at the time of insertion. FIG. 7 illustrates in cross section the combination of tube 11 with a light conductor 12' which has a bendable wire 22 extending the full length of the tube or at least a substantial portion of that length. The wire 22, formed of a bendable or ductile metal, may take a desired curvature and will tend to hold the light conductor and surrounding tube at that curvature in the absence of externally-applied re-forming forces.

FIGS. 8 and 9 illustrate a further embodiment which is similar to FIGS. 1–6 except that the distal end 12b" of conductor 12" is slightly enlarged and rounded, and substantially the entire length of the conductor (except for its distal end) is encased in a formable metal or plastic sleeve or sheath 23. Like wire 22, the sheath may take a desired curvature applied prior to or during insertion and maintain such curvature in the absence of externally-applied re-forming forces. The sheath may be formed of malleable stainless steel, aluminium, or any other material having similar properties. The ball-shaped end of the conductor preferably engages the inside surface of the tube (as shown) to assist in transmitting torquing forces during insertion of the conductor/tube combination.

While in the foregoing we have disclosed embodiments of the invention in considerable detail for purposes of illustration, it will be understood by those skilled in the art that many of these details may be varied without departing from the spirit and scope of the invention.

We claim:

1. A method for positioning a highly flexible medical tube of soft, transparent plastic material within a patient's body for the introduction or extraction of liquids into or from said body, said tube having a distal end and an open proximal end, comprising the steps of first stiffening said tube by inserting a flexible and bendable fiberoptic conductor that is stiffer than said tube into the tube's open proximal end and advancing said conductor until the tip thereof is located at the tube's distal end; coupling said proximal end of said tube to said conductor to prevent independent relative rotation of said conductor and tube; inserting the tube and conductor into a patient's body while directing light into said conductor to cause such light to be transmitted therethrough to the conductor's tip at the tube's distal end; locating the position of the tube's distal end as the tube is advanced by externally and visually observing light emitted from the tip of the conductor, and the tissues illuminated thereby, in the form of a spot of light projected through the skin of the patient; continuing to advance the tube and conductor with rotation thereof along a tortuous pathway within the patient's body until the spot of light is observed through the patient's skin to be located at a preselected position within the body; and thereafter uncoupling said conductor and tube and withdrawing the conductor from the proximal end of the medical tube with the distal end of the tube remaining at said predetermined position.

2. The method of claim 1 in which said medical tube includes a transversely-extending distal end wall; said light being directed through said end wall during said inserting, locating, and advancing steps.

3. The method for positioning a highly flexible medical tube of soft, transparent plastic material within a patient's body for the introducing or extracting liquids into or from said body, said tube having a distal end and an open proximal end and having disposed within the lumen thereof a flexible and bendable fiberoptic light conductor that is stiffer than said tube, said conductor having a tip located at the distal end of the tube and having a proximal end detachably coupled to said proximal end of said tube to secure the same together against independent relative rotation; comprising the steps of inserting said tube and conductor into a patient's body while directing light into said conductor to cause such light to be transmitted therethrough to the conductor's tip; locating the position of the tube's distal end as the tube and conductor are advanced by externally and visually observing light emitted from said tip in the form of a spot of light projected through the skin of the patient; continuing to advance the tube and conductor with rotation thereof along a tortuous pathway within the patient's body until the spot of light is observed through the patient's skin to be positioned at a predetermined location within the body; and thereafter uncoupling said conductor from said tube and withdrawing the conductor from the proximnal end of the tube while the distal end of said tube remains at said predetermined location.

4. The method of claim 3 in which said medical tube includes a distal end wall closing off the exteme distal end of said lumen; said light being directed through said end wall during said inserting, locating, and advancing steps.

5. The method of claim 3 in which said flexible conductor engages surfaces defining said lumen of said highly-flexible tube for transmitting torque from said conductor to said tube as said conductor and tube are rotated during said advancing steps.

6. In combination, a medical tube having a lumen of uniform diameter, an open proximal end, and a distal end provided with a transverse end wall; said tube being highly flexible and being formed of soft, transparent plastic material; and a tube-stiffening fiberoptic light conductor slidably and removably received in said lumen and having a proximal end provided with coupling means for releasably engaging the proximal end of said tube for securing the same against independent relative rotation; said conductor being flexible and bendable but having a flexibility substantially less, and a resistance to twisting substantially greater, than that of said tube and having a tip located at said distal end of said tube; and means provided by said conductor for operatively connecting the same to a source of light.

7. The combination of claim 6 in which said medical tube is provided with a plurality of sidewall openings adjacent the distal end thereof.

8. The combination of claim 6 in which said end wall has a rounded outer surface. Cancel claim 8 as unnecessary and without prejudice.

9. The combination of claim 6 in which said conductor has a rounded end face at said tip.

10. The combination of claim 6 in which said light conductor includes a bendable metallic wire extending a substantial distance along the length thereof.

11. The combination of claim 6 in which a bendable tubular sheath extends about said conductor along substantially the full length thereof; said sheath being manually formable and capable of maintaining selected longitudinal curvatures in said conductor and tube in the absence of externally-applied re-forming forces.

* * * * *